United States Patent [19]

Siddiqi et al.

[11] Patent Number: 4,937,186

[45] Date of Patent: Jun. 26, 1990

[54] METHOD FOR THE DETERMINATION OF BILIRUBIN IN SOLUTION

[76] Inventors: Iqbal Siddiqi, Tour de Champel 5, CH - 1206 Geneva; Ciaran Mangan, 103 Avenue Bois de la Chapelle, CH-1213 Onex, both of Switzerland

[21] Appl. No.: 149,548

[22] Filed: Jan. 28, 1988

[51] Int. Cl.$^5$ .......................... C12Q 1/28; C12Q 1/26
[52] U.S. Cl. .......................... 435/28; 435/25
[58] Field of Search ............... 435/25, 28, 4; 436/815, 436/150

[56] References Cited

U.S. PATENT DOCUMENTS

| | | | |
|---|---|---|---|
| 4,211,844 | 7/1980 | Wu | 435/25 |
| 4,353,983 | 10/1982 | Siddiqi | 435/28 X |
| 4,517,287 | 5/1985 | Scheibe et al. | 435/28 X |
| 4,571,383 | 2/1986 | Takayama et al. | 435/25 |
| 4,600,689 | 7/1986 | Matsui et al. | 435/25 |
| 4,607,010 | 8/1986 | Siddiqi et al. | 435/23 |
| 4,701,411 | 10/1987 | Wu | 435/25 |
| 4,781,890 | 11/1988 | Arai et al. | 435/805 |

FOREIGN PATENT DOCUMENTS

| | | | |
|---|---|---|---|
| 8100725 | 3/1981 | World Int. Prop. O. | 435/4 |
| 8605517 | 9/1986 | World Int. Prop. O. | |

*Primary Examiner*—Randall E. Deck
*Attorney, Agent, or Firm*—Davis Hoxie Faithfull & Hapgood

[57] ABSTRACT

A novel analytical method for bilirubin in biological fluids. Bilirubin is catalytically oxidized to biliverdin in the presence of bilirubin oxidase (BOX) and the latter is revertedly back-converted to initial bilirubin in the presence of suitable reducing agents. The corresponding oxidation of said reducing agents provides a signal which is monitored and provides the desired analytical data.

When using selected organic fluoro-compound, said signal is provided by the release of $F^-$ ions which can be measured electrometrically.

8 Claims, 1 Drawing Sheet

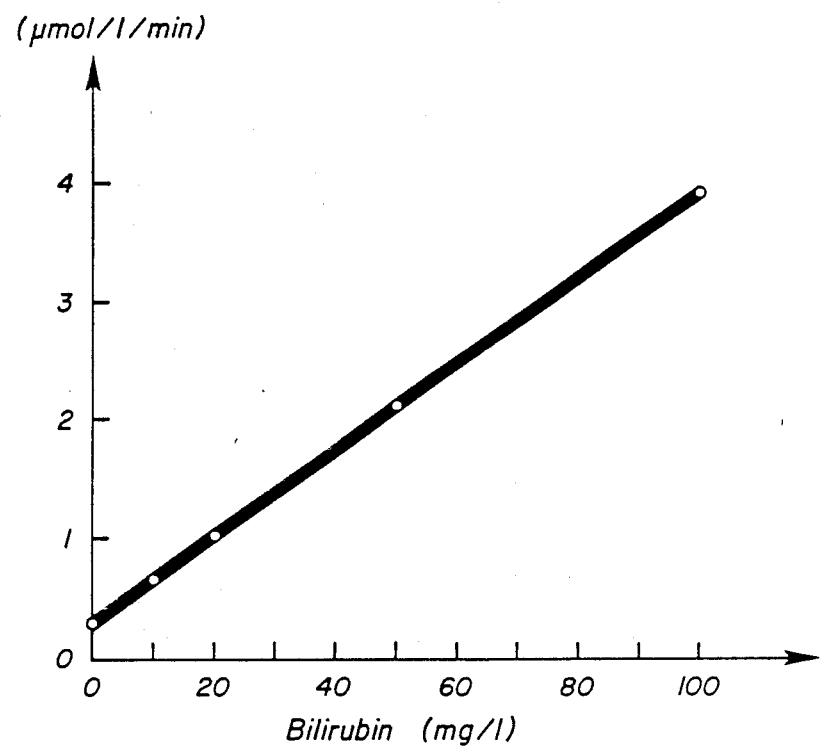

METHOD FOR THE DETERMINATION OF BILIRUBIN IN SOLUTION

The present invention relates to the determination of bilirubin in aqueous solutions, mostly in biological fluids.

A lot of literature already exists on the determination (detection, concentration measurement, etc.) of bilirubin for clinical and medical purposes. For instance, as reported in Patent Document DE-C-2.240.471; DE-A-2.007.013; DE-A-2.364.844 and DE-A-2.013.558, diazonium salts such as benzene-diazonium halides can be used. However, such reagents lack stability under usual temperature and humidity conditions and may become damaged on storage.

Other techniques for bilirubin determination involve its enzymically catalyzed air oxidation to biliverdin. Techniques of this kind have been reported in the following documents: R. BRODERSEN et al., European Journal of Biochemistry 10 (1969), 468; JP-Patent Publ. 11.194 (1983); JP-Patent Appln. 141.783 (1983), 1799 (1984) B. T. DOUMAS et al., Clin. Chem. 33 (1987), 1349–1353; C. J. P. MULLON et al., ibid, 1822–1825.

Bilirubin is a non-polar yellow pigment that occurs in blood plasma as a product of extra-cellular heme catabolism whereby the heme group of hemoglobin is enzymically oxidized to bilirubin. Water solubility of bilirubin is conferred by tight binding to albumin in the plasma and by conjugation to diglucuronides in the liver. The presence of abnormal levels of bilirubin in the plasma is an indication of liver diseases. The normal level is about 6–18 $\mu$mol/L (3.5–10 mg/L) almost entirely in the unconjugated form. The pigment is relatively stable in the dark under moisture free conditions. In solution however, and particularly in light, it oxidizes with time to biliverdin and therefore its concentration cannot be measured directly by measuring the absolute value of the optical density in the yellow band (e.g. 460 nm). Furthermore, when dealing with serum samples, direct measurement is further complicated by the presence of other compounds which absorb with variable intensities in the same or nearby ranges. Thus, for determining bilirubin optically in solutions, one must rely on rates of absorption changes, i.e. the rates at which the yellow color of bilirubin changes with time which depends, under known given conditions, upon the initial bilirubin concentration in a sample of serum (or other aqueous solution).

Yet, it is known that the oxidation by air of bilirubin (BR) to biliverdin (BV) is catalyzed by the presence of the enzyme bilirubin oxidase (BOX) which is obtained from some fungi and plants. Bilirubin oxidase (Enzyme Commission No. EC1.3.3.5) is a copper containing enzyme that has recently been used for the quantitative determination of bilirubin in plasma (GB-A-2,146,997). The enzyme can be extracted from many different types of plants and apparently exists in a number of types depending on the extraction methods. The products formed during the catalyzed oxidation of bilirubin to biliverdin ($H_2O_2$ or $H_2O$) depend on the type on BOX used. In the experiments reported here not all forms of BOX have been used. The preferred kind of BOX was derived from the fungus Myrothecium. The action of BOX has been demonstrated in the prior art by the rapid decrease, in the presence of the enzyme, of the absorption at 460 nm of BR solutions. This constitutes the basis of analytical bilirubin determination tests (see particularly GB-A-2,146,997 and related references cited therein). This test however has limitations in sensitivity and applicability, particularly when the solutions to be analyzed have inherent absorption in the 460 mm range, or if they lack transparency. Consequently, more versatile and sensitive methods are being continuously searched.

Moreover, as said before, the 460 nm test relies on measuring rates of decrease of absorbance values and this technique requires that special precautions be taken to protect the sample from degradation (i.e. premature oxidation) before the measurement is made and recorded. This is complicated and it would be much preferable if test conditions could be found in which the bilirubin sample will remain insensitive to oxidation and color changes, at least for a reasonable preliminary period during which the sample can be handled without special precautions to avoid fading of color.

The investigations of the present inventors led to the discovery disclosed herebelow which forms the basis of an entirely new method which cures the aforementioned deficiency and, moreover, has many advantages to be mentioned later.

This new analytical method for the determination of bilirubin in an aqueous solution comprises oxidizing bilirubin to biliverdin in the presence of bilirubin oxidase and an excess of reducing compound, which reducing compound is capable of reducing the biliverdin back to initial bilirubin, and then reducing the biliverdin to bilirubin in the presence of the reducing compound. The rate of consumption of the reducing compound is measured in order to determine the amount of bilirubin present in the aqueous solution. Where hydrogen peroxide is formed during the oxidation of bilirubin to biliverdin the method takes place in the substantial absence of peroxidase. Where hydrogen peroxide is not formed the method can take place in the presence or absence of peroxidase. The aqueous solution is preferably a biological fluid.

More specifically, it has been surprisingly found that in the BOX catalyzed reaction of BR to BV, the additional presence of selected reducing agent(s) (R) induces a fast reverse-reaction involving the back-conversion of biliverdin to bilirubin. Thus the present method relies on the occurence of a loop reaction and not only on a simple equilibrium strongly shifted to the left. This can be represented as follows:

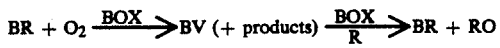

In this scheme "products" mean products of reduction of oxygen and RO means products of oxidation of R.

This scheme is backed-up, in addition to the substantially invariable 460 nm absorbance, by the observations that
(a) oxygen is indeed consumed in the reaction
(b) the eventual consumption of R, i.e. bilirubin is converted to biliverdin when R is exhausted.

Thus, with a given large starting excess of the reducing agent (R), the rate at which the latter is consumed is proportional to the amount of bilirubin (and hence also of biliverdin). Therefore, measuring the rate of consumption of R constitutes a versatile test for the determination of bilirubin in aqueous solutions and biological fluids.

One way to achieve this is to select R which, when in its oxidized form (RO), will provide a measurable signal.

Examples of such achievments are possible with systems or compounds whose standard redox potential is approximately between that of the ferrous/ferric couple and that of the $H^+/H_2$ couple, i.e. between approximatively 0.42 and –0.60 V at pH 7 (see Equilibria and Thermodynamics in Biochemical Transformations Biological Chemistry, H. R. Mahler and E. H. Cordes, Harper Internat. Ed. 1969, New York, London). Among such systems which may provide a color signal upon oxidation, the following can be cited: Cytochromes a and c, Ubiquinone, yellow enzyme FMN, riboflavin, $NAD^+$/NADH, Ferredoxin. A preferred compound is 4-aminoantypirin (4-AAP) which, upon oxidation, may couple with phenols and give colored complexes. This kind of measurement is actually conventional, for instance in the case of systems involving oxidases (e.g. glucose oxidase) which form hydrogen peroxide, the latter being determined in a peroxidase catalyzed oxidation of phenols. It is important to note that in the present system, many types of bilirubin oxidases are suitable, including those which operate without forming $H_2O_2$ in the air oxidation to biliverdin.

According to another approach, it has been found with surprise that if halogenated phenols or anilines are used in the presence of 4AAP, halides are liberated in proportion to the amount of bilirubin in the test. Suitable halogenated compounds (RHal) comprise 4-fluorophenol, 4-fluoroaniline, tetrafluoro-phenol and pentafluorophenol (defined as RF compounds).

The scheme for the key reaction is therefore as follows:

$$BV + RF \xrightarrow{BOX\ (4AAP)} BR + F^-$$

The liberation of $F^-$ is catalyzed by BOX and is very fast, therefore the rate of $F^-$ release is controlled by the oxidation of 4-AAP which itself depends on the initial concentration of the bilirubin.

$F^-$ can be measured by conventional means; one suitable means is to use an $F^-$ ion selective electrode.

The use of $F^-$ selective electrodes in biochemical reactions catalyzed by enzymes has been reported previously, see for instance U.S.-A-4,353,983; 4,607,010.

In the present invention, several types of bilirubin oxidase (BOX) are suitable including that extracted from various species of fungi, e.g. Schizophyllum, Trachyderma, Myrothercium (see for instance KOSAKA et al., Clin. Biochem. 16, Oct. 1983). In this invention BOX from Myrothercium Verucaria is preferred. Depending on the origin of BOX, the oxidation of BR may involve the formation of hydrogen peroxide or water as a byproduct; however the present method is operable whether $H_2O_2$ is formed or not. Moreover, in contrast to previous work (see U.S.-A-4,353,983) in which the liberation of $F^-$ ions from organic fluorocompounds was catalyzed by peroxidase, the addition of peroxidase to the present method has no discernable influence.

On a practical stand-point, the present method is carried out by measuring the release of $F^-$ from a sample of blood serum in a suitable buffer.

Briefly, a standard curve is preferably referred to in order to determine the release rate of $F^-$ ions after reaction of an unknown sample. A standard curve can be obtained by determining a set of samples containing known concentrations of bilirubin. The release rate of $F^-$ ions is recorded for each sample and the gradient of the kinetic curves is measured at a time (the same of course for each sample) when the system is stabilized and the rate curves are straight lines. It is noted that as long as the concentrations of the fluorocompound and 4AAP are in excess, the rate curve is a straight line (zero order reaction). The slopes are then shown on a graph in relation to the concentrations of bilirubin, so as to obtain a standard reference curve. The measured electrometric parameters used for preparing the kinetic curves can be the voltage readings of the electrometric system used together with the fluoride electrode (mV), or preferably the corresponding values of $[F^-]$ which can be calculated by the Nernst equation, which in the present case has the following form:

$$E = E_o - S \cdot \ln[F^-]$$

where E is the measured voltage and $E_o$ is an experimentally determined constant belonging to the system and including the activity factors and potentials of liquid junctions. S is the "Nernst gradient" which is a constant equal to about 57 mV in Tris buffer (in the cacodylate buffer at pH 7.0 the value is higher) for a variation of 10 units in the $F^-$ concentration, the latter being expressed in mmols/L. If the $[F^-]$ values calculated from the above relation and expressed in mg/L are used in the "charts", the resulting curves are near perfect straight lines and their gradient can be easily established.

The following examples illustrate the invention which is best understood with reference to the annexed drawings.

FIG. 1 is a calibration graph showing the slope of the rates of $F^-$ liberation against the concentration of bilirubin in standard aqueous solutions.

EXAMPLE 1

Preparation of bilirubin analysis calibration charts

The following reagent solutions were prepared in Tris buffer (200 mmol/L), pH 7, 5 $\mu$mol/L NaF:

(a) Bilirubin Standards: A stock solution containing 2.5 g/L was prepared in 10 mL of 100 mmol/L sodium carbonate solution. The following standards (expressed in mg/L) were prepared by dilution of the stock solution in distilled water: 10, 20, 40, 50, 100.

(b) Bilirubin Oxidase (BOX) Solution: A 2.5 mL solution containing 10 U/mL was prepared from a lyophilized commercial buffered preparation. Two commercial sources of BOX were used: (i) from Myrothecium Verucaria (Calbiochem #201105) and (ii) from Myrothecium Verucaria (Sigma #B0390). The Calbiochem reagent was preferred.

(c) Pentafluorophenol (PFP) Solution: 100 mmol/L in water.

(d) 4-Aminoantipyrine (4APP) Solution: 50 mmol/L in buffer Instrumentation: An Orion combination fluoride electrode (96-09) was used. The electrode was connected to a differential amplifier. The output of the amplifier was connected to Keithley 197 multimeter, interfaced via an IEEE 488 bus to an Apple II+computer for data acquisition. Experiments: Experiments were performed in Linbro tissue culture plates obtained from Flow Laboratories Ltd., Scotland. Each culture plate consists of 24 flat bottomed wells (17×16 mm) and a well capacity of 3.5 mL.

In a well of the Linbro plate the following reagent solutions were added: Tris buffer (500 μL), aminoantipyrine solution (10 μL), fluorophenol solution (50 μL), distilled water (370 μL). The fluoride electrode was lowered into the solution and the electrode potential allowed to stabilize (3–5 min). Following this 50 μL of a BOX solution was added and the electrode again allowed to stabilize (3–5 min). a bilirubin working standard solution (20 μL) was finally added to initiate the reaction. The $F^-$ liberation was monitored for 5 minutes. The rate of $F^-$ liberation in μmol/L.min was then calculated in the usual manner and the values found were plotted against the corresponding BR concentrations.

The slopes of the rates (in μmol/L.min) measured for standards of bilirubin containing 10, 20, 50 and 100 mg/L, as well as of a blank (zero bilirubin) are graphically depicted in FIG. 1.

It should be remarked that in these tests there was no change in the rate for about 20 min or more. Since the molar concentration of the fluorocompound and the 4AAP is about 1700 times greater than the bilirubin 100 mg/L standard and, since from the measured data the reaction rates are from about 0,5 to 4 μmol/min, there is now evidence that bilirubin is effectively converted to biliverdin only after the supply of reagents has become substantially exhausted. This surprising observation confirms that the rate determining step is the back-conversion of biliverdin to bilirubin in the presence of 4-AAP with consumption of the reducing agent. Evidence was also gained spectrophotometrically by showing that the absorption of the bilirubin at 460 nm does not substantially change in the BOX catalyzed oxidation in the presence of a reducing agent of the kind disclosed here. For instance, using a 50 mg/L solution of bilirubin in the presence of BOX, a variation of absorption of about 15% was observed over the first 10 min. In the presence of additional 4AAP, the variation in the same period was less than 2%.

It should also be noted that instead of pentafluorophenol other aromatic fluorine containing compounds with electron donating substituents can be used. Among such compounds, the following can be cited: 4-fluorophenol (FP), 4-fluoroaniline (FA) and tetrafluorophenol (TFP) can be used as well in the above test.

EXAMPLE 2

The method of example 1 was repeated under comparable condition and gave the following results expressed in μmol/L/min of released $F^-$ ions (mean of two results)

| Bilirubin standard (mg/L) | Results [$F^-$] (μmol/L/min) |
|---|---|
| 0 | 0,176 (noise) |
| 1,0 | 0,179 |
| 5,0 | 0,292 |
| 10,0 | 0,442 |
| 20,0 | 0,738 |
| 40,0 | 1,292 |

The above table was used as comparative data in the measurement of a normal serum (NS) and a pathological serum (PS) which were analyzed identically. The results NS 14 mg/L and PS 32 mg/L did correlate with the accepted values from usual methods.

EXAMPLE 3

The results of the previous example show that a non-zero reading of the electrometer is obtained even in the total absence of bilirubin (blank). Although this condition may become serious only with very low concentration of bilirubin, means to reduce the discrepancy were investigated, including varying the reaction medium and pH.

Thus, in addition to Tris-buffer (Tris=tris-(hydroxymethyl)-amino-methane) at pH 7, cacodylate (sodium dimethylarsinate) buffer at pH 7 and 5,5, as well as acetate buffer at pH 5,5 were investigated.

All three buffers were 0,1M and adjusted to the desired pH either with 0,1N NaOH or 0,1N acid (HCl was used for Tris and cacodylate, and acetic acid for acetate). The tests were run as in the previous examples using zero concentration of bilirubin (blanks) and 20 mg/L concentration.

The results for the blanks (i.e. zero bilirubin concentration) are shown in the table below and are expressed for convenience in percent of the value recorded for the corresponding 20 mg/L samples.

Two groups of results are given, one when using 4-fluorophenol as the reducing agent (4-FP), the other with 4-fluoroaniline (4-FA).

| Buffer (pH) | Results (%) | |
|---|---|---|
| | 4-FP | 4-FA |
| Tris (7) | 93 | 33 |
| Cacodylate (7) | 16 | 33 |
| " (5,5) | 9 | 20 |
| Acetate (5,5) | 25 | 50 |

The above data show that the least noise is experienced with cacodylate at pH 5,5. Also 4-FP gives a better response than 4-FA.

EXAMPLE 4

Experiments were also run to test the ability of several fluorocompounds in the present method. The tested compounds were 4-fluorophenol (4-FP), 4-fluoroaniline (4-FA) and pentafluorophenol (PFP). As in the previous examples, tests were run with zero bilirubin against a low concentration of bilirubin, i.e. 5 mg/L in this case. The buffer was cacodylate at pH 5,5 and 7. The results given below concern the zero bilirubin tests expressed as the % of the 5 mg/L tests.

| Fluorocompound | Results (%) at pH | |
|---|---|---|
| | 5.5 | 7 |
| 4-FP | 20 | 28 |
| 4-FA | 6,25 | 20 |
| PFP | 15 | 6 |

It should be noted that when the experiments disclosed in example 3 and 4 were run in the absence of 4-AAP (4-aminoantipyrine) only the back-ground noise was recorded, whatever the quantity of bilirubin.

It has been said before that the method of the present invention does not rely on the release of $F^-$ upon oxidation by the hydrogen peroxide which may form in the oxidation of bilirubin in the presence of some varieties of BOX. As said before, this was evidenced by using species of bilirubin oxidases not producing $H_2O_2$. Further checking was provided by operating in the presence (or in the absence) of a catalytic amount of horseradish peroxidase POD which is known (from previous work cited in this application and elsewhere) to catalyze the cleavage of the fluorine-carbon bond of organic fluoro-compounds by $H_2O_2$.

As in the previous examples, tests were run in pH 7 cacodylate buffer at zero and 5 mg/L bilirubin, in the presence (5 U/ml) or in the absence of POD.

Results, again referring to the zero test and expressed in % of the 5 mg/L test, showed that the presence of POD was immaterial. Thus with 4-FA the results were 23% (+POD) and 24% (no POD). With 4-FP, both results were 13%.

We claim:

1. A method for the determination of bilirubin in a biological fluid comprising the steps
   a. quantitatively oxidizing bilirubin to biliverdin in the presence of bilirubin oxidase,
   b. quantitatively reducing biliverdin by means of 4-aminoantipyrine in the presence of selected halogenated compounds, which selected halogenated compounds are capable of generating free halide ions in the presence of the oxidized form of 4-aminoantipyrine at a rate which is controlled by the rate of formation of the oxidized species of 4-aminoantipyrine, and wherein the 4-aminoantipyrine is used in molar excess relative to the bilirubin,
   c. measuring the rate of consumption of the 4-aminoantipyrine by analysing the rate of the formation of the halide ions in order to determine the amount of bilirubin present in the biological fluid, and wherein the rate of formation of said halide ions in the biological fluid is measured with an ion-selective electrode.

2. A method for the determination of bilirubin in an aqueous solution comprising the steps
   a. oxidizing bilirubin to biliverdin in the presence of bilirubin oxidase and an excess of 4-aminoantipyrine, which 4-aminoantipyrine is capable of reducing the biliverdin back to initial bilirubin,
   b. reducing the biliverdin to bilirubin in the presence of 4-aminoantipyrine and selected halogenated compounds, which selected halogenated comounds are capable of generating free halide ions in the presence of the oxidized form of 4-aminoantipyrine at a rate which is controlled by the rate of formation of the oxidized species of 4-aminoantipyrine,
   c. measuring the rate of formation of said halide ions with an ion selective electrode in order to determine the amount of bilirubin present in the aqueous solution,
   provided that where hydrogen peroxide is formed in step a, the method takes place in the substantial absence of peroxidase, further provided that where hydrogen peroxide is not formed in step a the method takes place in the presence or absence of peroxidase.

3. The method of claim 2 in which the halogenated compounds are selected from the group consisting of p-fluorophenol, p-fluoroaniline, tetrafluorophenol, pentafluorophenol and aromatic fluorine containing compounds having electron donating subsituents.

4. The method of claim 3 in which the halogenated compounds are selected from the group consisting of p-fluorophenol, p-fluoroniline, tetrafluorophenol, and pentafluorophenol.

5. The method of claim 3 wherein hydrogen peroxide is not formed in step a and the method takes place in the presence of peroxidase.

6. The method of claim 3 wherein hydrogen peroxide is not formed in step a and the method takes place in the absence of peroxidase.

7. The method of claim 3 wherein hydrogen peroxide is formed in step a and the method takes place in the absence of peroxidase.

8. The method of claim 3 wherein the bilirubin oxidase is derived from Myrothecium Verucaria.

* * * * *